(12) United States Patent
Zones et al.

(10) Patent No.: US 7,465,835 B2
(45) Date of Patent: *Dec. 16, 2008

(54) SYNTHESIS OF AMINES USING MOLECULAR SIEVE SSZ-75

(75) Inventors: Stacey Zones, San Francisco, CA (US); Allen Burton, Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/756,778

(22) Filed: Jun. 1, 2007

(65) Prior Publication Data

US 2007/0287867 A1   Dec. 13, 2007

Related U.S. Application Data

(60) Provisional application No. 60/804,254, filed on Jun. 8, 2006.

(51) Int. Cl.
*C07C 209/16* (2006.01)

(52) U.S. Cl. .............. 564/479; 564/474; 564/475; 564/480

(58) Field of Classification Search .............. None
See application file for complete search history.

(56) References Cited

U.S. PATENT DOCUMENTS

| | | | |
|---|---|---|---|
| 4,737,592 A | 4/1988 | Abrams et al. | |
| 4,910,006 A | 3/1990 | Zones et al. | |
| 5,166,111 A | 11/1992 | Zones et al. | |
| 5,268,161 A | 12/1993 | Nakagawa | |
| 5,316,753 A | 5/1994 | Nakagawa | |
| 2005/0042169 A1* | 2/2005 | Elomari | 423/706 |

OTHER PUBLICATIONS

S. B. Hong, et al., Synthesis, Structure Solution, Characterization, and Catalytic Properties of TNU-10: A High-Silica Zeolite with the STI Topology, Journal of The American Chemical Society, May 12, 2004, Paper No. 10.1021/ja031981t, pp. 5817-5826, vol. 126, Issue 18, American Chemical Society, Washington, D. C.

* cited by examiner

*Primary Examiner*—Brian J Davis
(74) *Attorney, Agent, or Firm*—Richard J. Sherida; Nirav Patel

(57) ABSTRACT

The present invention relates to new crystalline molecular sieve SSZ-75 having STI topology prepared using a tetramethylene-1,4-bis-(N-methylpyrrolidinium) dication as a structure-directing agent, and its use in catalysts for making amines.

6 Claims, No Drawings

SYNTHESIS OF AMINES USING MOLECULAR SIEVE SSZ-75

This application claims benefit under 35 USC 119 of Provisional Application 60/804,254, filed Jun. 8, 2006.

BACKGROUND OF THE INVENTION

1. Field of the Invention

The present invention relates to new crystalline molecular sieve SSZ-75, a method for preparing SSZ-75 using a tetramethylene-1,4-bis-(N-methylpyrrolidinium) dication as a structure directing agent ("SDA") and uses for SSZ-75.

2. State of the Art

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new molecular sieves with desirable properties for gas separation and drying, hydrocarbon and chemical conversions, and other applications. New molecular sieves may contain novel internal pore architectures, providing enhanced selectivities in these processes.

SUMMARY OF THE INVENTION

The present invention is directed to a family of crystalline molecular sieves with unique properties, referred to herein as "molecular sieve SSZ-75" or simply "SSZ-75". SSZ-75 has the framework topology designated "STI" by the IZA. Materials having the STI topology include naturally occurring stilbite and the zeolite designated TNU-10. Stilbite is disclosed in Breck, Zeolite Molecular Sieves, 1984, Robert E. Krieger Publishing Company where it is reported that stilbite has a typical silica/alumina mole ratio of 5.2. TNU-10 is reported in Hong et al., J. AM. CHEM. SOC. 2004, 126, 5817-5826 as having a silica/alumina mole ratio of about 14. When attempts were made to increase the silica/alumina mole ratio in the product, materials other than TNU-10 were produced.

In accordance with the present invention there is provided a process for producing methylamine or dimethylamine comprising reacting methanol, dimethyl ether or a mixture thereof and ammonia in the gaseous phase in the presence of a catalyst comprising a crystalline molecular sieve having STI topology and having a mole ratio of 15 and greater of (1) an oxide of a first tetravalent element to (2) an oxide of a trivalent element, pentavalent element, second tetravalent element which is different from said first tetravalent element or mixture thereof. The molecular sieve can have a mole ratio of 15 and greater of (1) silicon oxide to (2) an oxide selected from aluminum oxide, gallium oxide, iron oxide, boron oxide, titanium oxide, indium oxide and mixtures thereof. The molecular sieve has, after calcination, the X-ray diffraction lines of Table II.

DETAILED DESCRIPTION OF THE INVENTION

The present invention comprises a molecular sieve designated herein "molecular sieve SSZ-75" or simply "SSZ-75".

In preparing SSZ-75, a tetramethylene-1,4-bis-(N-methylpyrrolidinium) dication is used as a structure directing agent ("SDA"), also known as a crystallization template. The SDA useful for making SSZ-75 has the following structure:

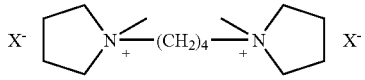

Tetramethylene-1,4-bis-(N-methylpyrrolidinium) dication

The SDA dication is associated with anions ($X^-$) which may be any anion that is not detrimental to the formation of the SSZ-75. Representative anions include halogen, e.g., fluoride, chloride, bromide and iodide, hydroxide, acetate, sulfate, tetrafluoroborate, carboxylate, and the like. Hydroxide is the most preferred anion. The structure directing agent (SDA) may be used to provide hydroxide ion. Thus, it is beneficial to ion exchange, for example, a halide to hydroxide ion.

The tetramethylene-1,4-bis-(N-methylpyrrolidinium) dication SDA can be prepared by a method similar to that described in U.S. Pat. No. 5,166,111, issued Nov. 24, 1992 to Zones et al., which discloses a method for preparing a bis(1,4-diazoniabicyclo[2.2.2]alpha, omega alkane compound, or U.S. Pat. No. 5,268,161, issued Dec. 7, 1993, which discloses a method for preparing 1,3,8,8-pentamethyl-3-azoniabicyclo[3.2.1]octane cation. U.S. Pat. No. 5,166,111 and U.S. Pat. No. 5,268,161 are incorporated by reference herein in their entirety.

In general, SSZ-75 is prepared by contacting (1) an active source(s) of silicon oxide, and (2) an active source(s) of aluminum oxide, gallium oxide, iron oxide, boron oxide, titanium oxide, indium oxide and mixtures thereof with the tetramethylene-1,4-bis-(N-methylpyrrolidinium) dication SDA in the presence of fluoride ion.

SSZ-75 is prepared from a reaction mixture comprising, in terms of mole ratios, the following:

TABLE A

| Reaction Mixture | |
|---|---|
| $SiO_2/X_aO_b$ | at least 15 (i.e., 15-infinity) |
| $OH^-/SiO_2$ | 0.20-0.80 |
| $Q/SiO_2$ | 0.20-0.80 |
| $M_{2/n}/SiO_2$ | 0-0.04 |
| $H_2O/SiO_2$ | 2-10 |
| $HF/SiO_2$ | 0.20-0.80 | where X is aluminum, gallium, iron, boron, titanium, indium and mixtures thereof, a is 1 or 2, b is 2 when a is 1 (i.e., W is tetravalent); b is 3 when a is 2 (i.e., W is trivalent), M is an alkali metal cation, alkaline earth metal cation or mixtures thereof; n is the valence of M (i.e., 1 or 2); Q is a tetramethylene-1,4-bis-(N-methylpyrrolidinium) dication and F is fluoride.

As noted above, the $SiO_2/X_aO_b$ mole ratio in the reaction mixture is $\geq 15$. This means that the $SiO_2/X_aO_b$ mole ratio can be infinity, i.e., there is no $X_aO_b$ in the reaction mixture. This results in a version of SSZ-75 that is essentially all silica. As used herein, "essentially all silicon oxide" or "essentially all-silica" means that the molecular sieve's crystal structure is comprised of only silicon oxide or is comprised of silicon oxide and only trace amounts of other oxides, such as aluminum oxide, which may be introduced as impurities in the source of silicon oxide.

In practice, SSZ-75 is prepared by a process comprising.
  (a) preparing an aqueous solution containing (1) a source(s) of silicon oxide, (2) a source(s) of aluminum oxide, gallium oxide, iron oxide, boron oxide, titanium oxide, indium oxide and mixtures thereof, (3) a source of fluoride ion and (4) a tetramethylene-1,4-bis-(N-methylpyrrolidinium) dication having an anionic counterion which is not detrimental to the formation of SSZ-75;

(b) maintaining the aqueous solution under conditions sufficient to form crystals of SSZ-75; and (c) recovering the crystals of SSZ-75.

The reaction mixture is maintained at an elevated temperature until the crystals of the SSZ-75 are formed. The hydrothermal crystallization is usually conducted under autogenous pressure, at a temperature between 100° C. and 200° C. preferably between 135° C. and 180° C. The crystallization period is typically greater than 1 day and preferably from about 3 days to about 20 days. The molecular sieve may be prepared using mild stirring or agitation.

During the hydrothermal crystallization step, the SSZ-75 crystals can be allowed to nucleate spontaneously from the reaction mixture. The use of SSZ-75 crystals as seed material can be advantageous in decreasing the time necessary for complete crystallization to occur. In addition, seeding can lead to an increased purity of the product obtained by promoting the nucleation and/or formation of SSZ-75 over any undesired phases. When used as seeds, SSZ-75 crystals are added in an amount between 0.1 and 10% of the weight of the first tetravalent element oxide, e.g. silica, used in the reaction mixture.

Once the molecular sieve crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized SSZ-75 crystals. The drying step can be performed at atmospheric pressure or under vacuum.

SSZ-75 as prepared has the X-ray diffraction lines of Table I below. SSZ-75 has a composition, as synthesized (i.e. prior to removal of the SDA from the SSZ-75) and in the anhydrous state, comprising the following (in terms of mole ratios):

| | |
|---|---|
| $SiO_2/X_cO_d$ | at least 15 (i.e., 15-infinity) |
| $M_{2/n}/SiO_2$ | 0-0.03 |
| $Q/SiO_2$ | 0.02-0.08 |
| $F/SiO_2$ | 0.01-0.04 | wherein X is aluminum, gallium, iron, boron, titanium, indium and mixtures thereof, c is 1 or 2; d is 2 when c is 1 (i.e., W is tetravalent) or d is 3 or 5 when c is 2 (i.e., d is 3 when W is trivalent or 5 when W is pentavalent), M is an alkali metal cation, alkaline earth metal cation or mixtures thereof; n is the valence of M (i.e., 1 or 2); Q is a tetramethylene-1,4-bis-(N-methylpyrrolidinium) dication and F is fluoride.

SSZ-75 (whether in the as synthesized or calcined version) has a $SiO_2/X_cO_d$ mole ratio of at least 15 (i.e., 15-infinity), for example 20-infinity or 40-infinity.

SSZ-75 has the STI framework topology. It is characterized by its X-ray diffraction pattern. SSZ-75 as-synthesized, has a crystalline structure whose X-ray powder diffraction pattern exhibits the characteristic lines shown in Table I.

TABLE I

As-Synthesized SSZ-75

| 2 Theta | d-spacing (Angstroms) | Relative Integrated Intensity (%) |
|---|---|---|
| 10.04 | 8.80 | VS |
| 17.17 | 5.16 | W |
| 19.44 | 4.56 | S |
| 21.13 | 4.20 | W-M |
| 22.36 | 3.97 | VS |
| 22.49 | 3.95 | M |
| 24.19 | 3.68 | W |
| 26.61 | 3.35 | W |
| 28.49 | 3.13 | W |
| 30.20 | 2.96 | M |

(a)±0.1
(b)The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

Table IA below shows the X-ray powder diffraction lines for as-synthesized SSZ-75 including actual relative intensities.

TABLE IA

As-Synthesized SSZ-75

| 2 Theta | d-spacing (Angstroms) | Relative Integrated Intensity (%) |
|---|---|---|
| 9.84 | 8.98 | 7 |
| 10.04 | 8.80 | 100 |
| 13.24 | 6.68 | 7 |
| 14.19 | 6.24 | 4 |
| 17.17 | 5.16 | 13 |
| 19.44 | 4.56 | 47 |
| 20.01 | 4.43 | 2 |
| 20.17 | 4.40 | 7 |
| 21.13 | 4.20 | 21 |
| 22.36 | 3.97 | 84 |
| 22.49 | 3.95 | 38 |
| 24.19 | 3.68 | 12 |
| 26.13 | 3.41 | 7 |
| 26.61 | 3.35 | 17 |
| 28.49 | 3.13 | 18 |
| 29.31 | 3.04 | 10 |
| 30.20 | 2.96 | 30 |
| 30.30 | 2.95 | 7 |
| 31.94 | 2.80 | 2 |
| 32.12 | 2.78 | 1 |
| 32.61 | 2.74 | 3 |
| 33.13 | 2.70 | 4 |
| 33.59 | 2.67 | 6 |
| 34.86 | 2.57 | 7 |
| 35.13 | 2.55 | 5 |
| 35.75 | 2.51 | 6 |
| 36.55 | 2.46 | 2 |
| 36.69 | 2.45 | 1 |
| 37.19 | 2.42 | 1 |

(a)±0.1

After calcination, the X-ray powder diffraction pattern for SSZ-75 exhibits the characteristic lines shown in Table II below.

TABLE II

Calcined SSZ-75

| 2 Theta | d-spacing (Angstroms) | Relative Integrated Intensity (%) |
|---|---|---|
| 9.64 | 9.17 | W |
| 9.95 | 8.88 | VS |

TABLE II-continued

Calcined SSZ-75

| 2 Theta | d-spacing (Angstroms) | Relative Integrated Intensity (%) |
|---|---|---|
| 10.06 | 8.79 | M |
| 13.14 | 6.73 | W |
| 19.38 | 4.58 | W |
| 21.03 | 4.22 | W |
| 22.35 | 3.97 | M-S |
| 24.19 | 3.68 | W |
| 28.37 | 3.14 | W |
| 30.16 | 2.96 | W |

(a) ±0.1

Table IIA below shows the X-ray powder diffraction lines for calcined SSZ-75 including actual relative intensities.

TABLE IIA

Calcined SSZ-75

| 2 Theta | d-spacing (Angstroms) | Relative Integrated Intensity (%) |
|---|---|---|
| 9.64 | 9.17 | 8 |
| 9.95 | 8.88 | 100 |
| 10.06 | 8.79 | 24 |
| 13.14 | 6.73 | 7 |
| 14.17 | 6.25 | 2 |
| 17.13 | 5.17 | 2 |
| 17.25 | 5.14 | 3 |
| 19.38 | 4.58 | 15 |
| 20.23 | 4.39 | 1 |
| 21.03 | 4.22 | 10 |
| 22.35 | 3.97 | 39 |
| 22.54 | 3.94 | 6 |
| 24.19 | 3.68 | 7 |
| 25.24 | 3.53 | 6 |
| 26.08 | 3.41 | 2 |
| 26.48 | 3.36 | 6 |
| 28.37 | 3.14 | 7 |
| 29.25 | 3.05 | 3 |
| 30.16 | 2.96 | 13 |
| 30.32 | 2.95 | 2 |
| 32.18 | 2.78 | 1 |
| 33.02 | 2.71 | 2 |
| 33.54 | 2.67 | 2 |
| 34.57 | 2.59 | 1 |
| 34.94 | 2.57 | 2 |
| 35.09 | 2.56 | 1 |
| 35.68 | 2.51 | 2 |
| 36.58 | 2.45 | 1 |
| 37.07 | 2.42 | 1 |

(a) ±0.1

The X-ray powder diffraction patterns were determined by standard techniques. The radiation was CuKalpha radiation. The peak heights and the positions, as a function of 2θ where θ is the Bragg angle, were read from the relative intensities of the peaks, and d, the interplanar spacing in Angstroms corresponding to the recorded lines, can be calculated.

The variation in the scattering angle (two theta) measurements, due to instrument error and to differences between individual samples, is estimated at ±0.1 degrees.

Representative peaks from the X-ray diffraction pattern of as-synthesized SSZ-75 are shown in Table I. Calcination can result in changes in the intensities of the peaks as compared to patterns of the "as-synthesized" material, as well as minor shifts in the diffraction pattern.

Crystalline SSZ-75 can be used as-synthesized, but preferably will be thermally treated (calcined). Usually, it is desirable to remove the alkali metal cation (if any) by ion exchange and replace it with hydrogen, ammonium, or any desired metal ion. Calcined SSZ-75 has an n-hexane adsorption capacity of about 0.15 cc/g.

SSZ-75 can be formed into a wide variety of physical shapes. Generally speaking, the molecular sieve can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the SSZ-75 can be extruded before drying, or, dried or partially dried and then extruded.

SSZ-75 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa, both of which are incorporated by reference herein in their entirety.

SSZ-75 is useful as an adsorbent for gas separations (owing to its high pore volume while maintaining diffusion control and hydrophobicity). SSZ-75 can also be used in a catalyst for converting oxygenates (such as methanol) to olefins, and for making small amines. SSZ-75 can be used to reduce oxides of nitrogen in gas streams (such as automotive exhaust). SSZ-75 can also be used as a cold start hydrocarbon trap in combustion engine pollution control systems. SSZ-75 is particularly useful for trapping $C_3$ fragments.

The molecular sieve of the present invention can be used in a catalyst to prepare methylamine or dimethylamine. Dimethylamine is generally prepared in industrial quantities by continuous reaction of methanol (and/or dimethylether) and ammonia in the presence of a silica-alumina catalyst. The reactants are typically combined in the vapor phase, at temperatures in the range of 300° C. to 500° C., and at elevated pressures. Such a process is disclosed in U.S. Pat. No. 4,737,592, issued Apr. 12, 1988 to Abrams et al., which is incorporated by reference in its entirety.

The catalyst is used in its acid form. Acid forms of molecular sieves can be prepared by a variety of techniques. Preferably, the molecular sieve used to prepare dimethylamine will be in the hydrogen form, or have an alkali or alkaline earth metal, such as Na, K, Rb, or Cs, ion-exchanged into it.

The process of the present invention involves reacting methanol, dimethylether or a mixture thereof and ammonia in amounts sufficient to provide a carbon/nitrogen (C/N) ratio from about 0.2 to about 1.5, preferably about 0.5 to about 1.2. The reaction is conducted at a temperature from about 250° C. to about 450° C., preferably about 300° C. to about 400° C. Reaction pressures can vary from about 7-7000 kPa (1-1000 psi), preferably about 70-3000 kPa (10-500 psi). A methanol and/or dimethylether space time of about 0.01-80 hours, preferably 0.10-1.5 hours, is typically used. This space time is calculated as the mass of catalyst divided by the mass flow rate of methanol/dimethylether introduced into the reactor.

EXAMPLES

The following examples demonstrate but do not limit the present invention.

Example 1

Synthesis of Al-Containing SSZ-75

1.5 mM of tetramethylene-1,4-bis-(N-methylpyrrolidinium) dication SDA (3 mM OH−) was mixed in a Teflon cup (for a Parr 23 ml reactor) with 1.26 grams of tetraethylorthosilicate and the cup was placed in a hood to evaporate (as ethanol is formed from hydrolysis) over several days. When all of the visible liquid was gone, the Teflon cup was reweighed and water was added to bring the $H_2O/SiO_2$ mole ratio to about four. Then, 12 mg of Reheiss F2000 (50% $Al_2O_3$) was added and dissolved into the reaction mixture. This represents a starting synthesis mole ratio of $SiO_2/Al_2O_3$ of 100. Lastly, 0.135 gram of 50% HF was added using a plastic pipette. The get was mixed with a plastic spatula and then the resulting reaction mixture was heated in a closed vessel rotating at 43 RPM at 150° C. for 16 days. A crystalline product formed which was recovered and found by X-ray diffraction analysis to be molecular sieve SSZ-75.

Example 2

Synthesis of Al-Containing SSZ-75

The procedure described in Example 1 was repeated, except that the source of aluminum was LZ-210 zeolite (a form of dealuminated FAU) and the $SiO_2/Al_2O_3$ mole ratio was 70. The reaction formed SSZ-75 in 10 days.

Example 3

Synthesis of Al-Containing SSZ-75

The procedure described in Example 1 was repeated, except that the source of aluminum was Catapal B (a form of pseudoboehmite alumina). The reaction formed SSZ-75 in 10 days.

Examples 4-7

Synthesis of All-Silica SSZ-75

A procedure similar to that of Example 1 was repeated using the reaction mixture (expressed as mole ratios) and conditions shown in the table below. The reactions were run until a crystalline product was observed by SEM, and then the product was recovered. The products are also shown in the table.

| Ex. | SDA/$SiO_2$ | $NH_4F/SiO_2$ | $HF/SiO_2$ | $H_2O/SiO_2$ | ° C./RPM | Prod. |
|---|---|---|---|---|---|---|
| 4 | 0.50 | 0.0 | 0.50 | 5.0 | 150/43 | SSZ-75 |
| 5 | 0.40 | 0.1 | 0.40 | 5.0 | 150/43 | SSZ-75 |
| 6 | 0.30 | 0.2 | 0.30 | 5.0 | 150/43 | MTW |
| 7 | 0.20 | 0.3 | 0.20 | 5.0 | 150/43 | Amor. ZSM-48 |

Example 8

Calcination of SSZ-75

The product from Example 1 was calcined in the following manner. A thin bed of material was heated in a flowing bed of air in a muffle furnace from room temperature to 120° C. at a rate of 1° C. per minute and held at 120° C. for two hours. The temperature is then ramped up to 540° C. at the same rate and held at this temperature for three hours, after which it was increased to 594° C. and held there for another three hours.

Example 9

Conversion of Methanol

The calcined material of Example 8 (0.10) gram was pelleted and meshed (with recycling) to 20-40 mesh and packed into a ⅜ inch stainless steel reactor. After sufficient purge with nitrogen carrier gas (20 cc/min), the catalyst was heated to 750° F. (399° C.). A feed of 22.5% methanol in water was introduced into the reactor via syringe pump at a rate of 1.59 cc/hr. A sample of the effluent stream was diverted to an on-line gas chromatograph at ten minute point of feed introduction. SSZ-75 showed the following behavior:

Methanol conversion=100%

No dimethylether detected $C_2$-$C_4$ is about 70% of the product $C_{5+}$ showed a mixture of olefins and saturates Aromatics were made with ethylbenzene the most abundant single product Trimethylbenzene isomers were observed as the heaviest products At 100 minutes on stream the SSZ-75 was fouling, but still produced the same products (although very few aromatics were observed).

What is claimed is:

1. A process for producing methylamine or dimethylamine comprising reacting methanol, dimethyl ether or a mixture thereof and ammonia in the gaseous phase in the presence of a catalyst comprising a crystalline molecular sieve having STI topology and having a mole ratio of at least 15 of (1) an oxide of a first tetravalent element to (2) an oxide of a trivalent element, pentavalent element, second tetravalent element which is different from said first tetravalent element or mixture thereof.

2. The process of claim 1 wherein the molecular sieve has a mole ratio of at least 15 of (1) silicon oxide to (2) an oxide selected from aluminum oxide, gallium oxide, iron oxide, boron oxide, titanium oxide, indium oxide and mixtures thereof.

3. The process of claim 1 wherein the molecular sieve has, after calcination, the X-ray diffraction lines as shown below:

| 2 Theta | d-spacing (Angstroms) | Relative Integrated Intensity (%) |
|---|---|---|
| 9.64 | 9.17 | W |
| 9.95 | 8.88 | VS |
| 10.06 | 8.79 | M |
| 13.14 | 6.73 | W |
| 19.38 | 4.58 | W |
| 21.03 | 4.22 | W |
| 22.35 | 3.97 | M-S |
| 24.19 | 3.68 | W |
| 28.37 | 3.14 | W |
| 30.16 | 2.96 | W |

[a]±0.1.

4. The process of claim 2 wherein the molecular sieve has, after calcination, the X-ray diffraction lines as shown below:

| 2 Theta | d-spacing (Angstroms) | Relative Integrated Intensity (%) |
|---|---|---|
| 9.64 | 9.17 | W |
| 9.95 | 8:88 | VS |
| 10.06 | 8.79 | M |
| 13.14 | 6.73 | W |
| 19.38 | 4.58 | W |
| 21.03 | 4.22 | W |
| 22.35 | 3.97 | M-S |
| 24.19 | 3.68 | W |

-continued

| 2 Theta | d-spacing (Angstroms) | Relative Integrated Intensity (%) |
|---|---|---|
| 28.37 | 3.14 | W |
| 30.16 | 2.96 | W. |

5. The process of claim 2 wherein the methanol, dimethylether or mixture thereof and ammonia are present in amounts sufficient to provide a carbon/nitrogen ratio from about 0.2 to about 1.5.

6. The process of claim 2 conducted at a temperature of from about 250° C. to about 450° C.

\* \* \* \* \*